(12) United States Patent
Kang et al.

(10) Patent No.: US 7,094,407 B2
(45) Date of Patent: Aug. 22, 2006

(54) FUSION PEPTIDE CONTAINING HUMAN TYPE-1 COLLAGEN DERIVED PEPTIDE, PREPARATION THEREOF, AND SKIN ANTI-AGING COSMETIC COMPOSITION COMPRISING THE SAME

(75) Inventors: Nae-Gyu Kang, Daejeon (KR);
Young-Sook Song, Daejeon (KR);
Sun-Gyoo Park, Daejeon (KR);
Yong-Hwa Lee, Daejeon (KR);
Wan-Goo Cho, Daejeon (KR);
Seh-Hoon Kang, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 489 days.

(21) Appl. No.: 10/243,836

(22) Filed: Sep. 16, 2002

(65) Prior Publication Data

US 2003/0185862 A1 Oct. 2, 2003

(30) Foreign Application Priority Data

Mar. 15, 2002 (KR) .............................. 2002-14063

(51) Int. Cl.
*A61K 39/00* (2006.01)
*A61K 38/04* (2006.01)
*C12P 21/06* (2006.01)

(52) U.S. Cl. ................. 424/192.1; 435/69.1; 530/327; 530/328; 514/14; 514/16; 514/844; 514/947

(58) Field of Classification Search ............. 424/192.1; 435/69.1, 69.7; 530/327, 328, 330, 334; 514/14, 16, 17, 844, 946, 947

See application file for complete search history.

(56) References Cited

U.S. PATENT DOCUMENTS 6,444,647 B1 * 9/2002 Robinson et al. ............. 514/17

6,620,419 B1 * 9/2003 Lintner ....................... 424/401

FOREIGN PATENT DOCUMENTS

| CA | 2094658 A1 | 10/1993 |
| WO | WO 97/18235 A1 | 5/1997 |
| WO | WO 00/15188 A1 | 3/2000 |

OTHER PUBLICATIONS

Schwarze et al., Science, vol. 285, No. 5433, pp. 1569-1572 (1999).
Fawell et al., Cell Biology, vol. 91, pp. 664-668 (Jan. 1994).
Singh et al., Proceed. Intern. Symp. Control. Ref. Bioact. Mater., vol. 20, pp. 107-108, (1993).
Jin et al., Free Radical Biology & Medicine, vol. 31, No. 11, pp. 1509-1519 (2001).
Abstract of JP 2001-163758 A2, Jun. 19, 2001.
Abstract of JP 10-298196 A2, Nov. 10, 1998.
Abstract of JP 09-295930 A2, Nov. 18, 1997.
Abstract of JP 04-090844 A2, Mar. 24, 1992.

* cited by examiner

Primary Examiner—Jon Weber
Assistant Examiner—Abdel A. Mohamed
(74) Attorney, Agent, or Firm—Birch Stewart Kolasch & Birch LLP

(57) ABSTRACT

The present invention relates to a fusion peptide, in which a self cell-penetrating Tat peptide having a self penetrating signal is bound to a human Type-I collagen C-terminal derived peptide, a preparation thereof, and a skin anti-aging cosmetic composition comprising the same. Since the fusion peptide, in which the Tat peptide is bound to the human Type-collagen C-terminal derived peptide is highly stable and has a superior skin absorption capability, the present invention provides a skin anti-aging agent having superior synthesis of collagen and hyaluronic acid, anti-aging effects, and improved durability of the effects.

7 Claims, No Drawings

FUSION PEPTIDE CONTAINING HUMAN TYPE-1 COLLAGEN DERIVED PEPTIDE, PREPARATION THEREOF, AND SKIN ANTI-AGING COSMETIC COMPOSITION COMPRISING THE SAME

BACKGROUND OF THE INVENTION (a) Field of the Invention

The present invention relates to a fusion peptide, in which a self cell-penetrating Tat peptide (transactivator of transcription peptide) is bound to a human Type-collagen C-terminal derived peptide, and to a skin anti-aging cosmetic composition comprising the same.

(b) Description of the Related Art

Collagen is an important structural ingredient of extra-cellular matrix accounting for 25% of the total protein in mammals. The abnormal synthesis and analysis of collagen is closely related to skin aging, particularly the formation of wrinkles. It has been reported that a type-I collagen is an important structural ingredient of extra-cellular matrix in skin, bones, etc. in that it controls collagen synthesis inside cells in a cell synthesized collagen (Wiestner, M. et al. (1979) *J. Biol. Chem.* 254, 10482 10484, Paglia, L. M. et al. (1979) Biochemistry 18, 5030 5034). If a part of a peptide of human α1(I) procollagen C-terminal is added to human fibroblast, a synthesis of type-III collagen and fibronectin is strengthened [K. Katayama et al.(1991), Biochemistry, 30, 7097, K. Katayama et al.(1993), *J. Biol. Chem.* 268(14), 9941, Aycock, R. S. et. al.(1986), *J. Biol. Chem.* 261, 14355]. it was determined from this report that a human type-collagen derived peptide may provide anti-aging effects. That is, if a part of human Type-collagen transmits on a fibroblast, cell-growth and creation of extra-cellular matrix will be promoted by collagen synthesis. Therefore, through the synthesis of various peptides and screening, it has been verified that peptides of amino sequences 182 to 216, and 197 to 241 of human Type-collagen are effective in preventing aging of the skin by using a collagen synthesis process (PCT/FR99/02178, WO 00/15188). However, these peptides have weak skin absorbency due to their water-solubility and thus anti-aging effects of the skin are not to be expected. Therefore, there is an urgent need for the development of a novel skin anti-aging agent that has increased skin absorbency to thereby maximize anti-aging effects.

As one method for increasing skin absorbency of these peptide anti-aging agents, a method of grafting a long chain fatty acid such as palmitic acid on a peptide has been suggested in order to increase the fat solubility of the peptide (France Patent Application No. 2788058, PCT Laid-open Publication No. WO 00/40611). However, skin absorbency is not significantly improved with this method.

Accordingly, there is a need for the development of a novel skin anti-aging agent that does not cause skin irritation and that has increased skin absorbency, improved stability, and provides maximum anti-aging effects to the skin.

SUMMARY OF THE INVENTION

In order to solve these problems of the prior art, it is an object of the present invention to provide a fusion peptide, in which a Tat peptide having a self cell-penetration property is bound to a human Type-collagen C-terminal derived peptide, the resulting peptide being such that it does not cause irritation, easily and safely penetrates into the integument and endothelium, does not cause skin disease, and has superior and continuous skin anti-aging effects by synthesis of collagen and hyaluronic acid.

It is another object of the present invention to provide a method for preparing a fusion peptide, in which a self cell-penetrating Tat peptide is bound to a human Type-collagen C-terminal derived peptide.

It is yet another object of the present invention to provide a skin anti-aging cosmetic composition comprising a fusion peptide, in which a self cell-penetrating Tat peptide is bound to a human Type-collagen C-terminal derived peptide, the cosmetic composition having superior cell-penetration properties and synthesis of collagen and hyaluronic acid, anti-aging effects, and is durable.

In order to achieve these objects, the present invention provides a fusion peptide, in which a Tat peptide having a self cell-penetration property is bound to a human Type-collagen C-terminal derived peptide (Tat-human Type-collagen DP):

[Chemical Formula 1]

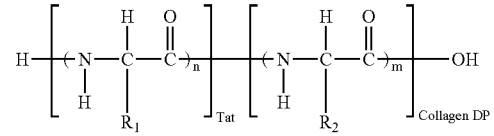

where $[\ ]_{Tat}$ is a Tat peptide having a self cell-penetration property; $R_1$ is one or more substituent selected from the group consisting of side chains of glutamine, lysine, arginine, and glycine; and n is an integer from 4 to 12; and $[\ ]_{collagen\ DP}$ is a peptide of continuous 5 to 35 amino acids consisting of a peptide of amino acids 212 to 216 in a peptide of amino acids 182 to 246 of human type-I collagen shown in SEQ ID NO:1; $R_2$ is a side chain of amino acids comprising the peptide; and m is an integer from 5 to 35.

DETAILED DESCRIPTION AND THE PREFERRED EMBODIMENTS

The present invention will now be explained in detail.

The present invention provides a fusion peptide, in which a Tat peptide having a self cell-penetration property is bound to a peptide derived from human Type-collagen C-terminal, represented by the following Chemical Formula 1 (Tat-human Type-collagen DP):

[Chemical Formula 1]

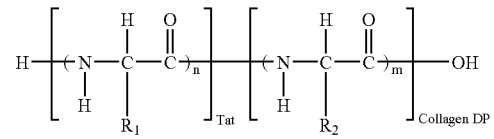

In the formula, $[\ ]_{Tat}$ is a Tat peptide having a self cell-penetration property; the Chemical Formula in $(\ )_n$ represents an amino acid sequence; $R_1$ is one or more substituent selected from the group consisting of side chains of glutamine, lysine, arginine, and glycine; and n is an integer from 4 to 12.

Further, $[\ ]_{collagen\ DP}$ is a peptide derived from human type-I collagen C-terminal consisting of a peptide of continuous 5 to 35 amino acids consisting a peptide of amino acids 212 to 216 in a peptide of amino acids 182 to 246 of human type-I collagen shown in SEQ ID NO:1, and preferably an 8 to 15 peptide comprising a peptide of SEQ ID NO:2, and more preferably, a peptide of SEQ ID NO:2 (m=5), a peptide of Sequence No. 3 (m=7), or a peptide of SEQ ID NO:4 (m=11); $R_2$ is a side chain of an amino acid of the peptide; and m is an integer from 5 to 35.

The sequence of amino acids 182 to 246 of the human type-I collagen is as follows, and it is also shown in SEQ ID NO:1:

N-Ala-Glu-Gly-Asn-Ser-Arg-Phe-Thr-Tyr-Ser-Val-Thr-Val-Asp-Gly-Cys-Thr-Ser-His-Thr-Gly-Ala-Trp-Gly-Lys-Thr-Val-Ile-Glu-Tyr-Lys-Thr-Thr-Lys-Ser-Ser-Arg-Leu-Pro-Ile-Ile- Asp-Val-Ala-Pro-Leu-Asp-Val-Gly-Ala-Pro-Asp-Gln-Glu-Phe-Gly-Phe-Asp-Val-Gly-Pro-Val-Cys-Phe-Leu-C.

The sequence of amino acids 212 to 216 of the human type-I collagen C-terminal is as follows, and is also shown in SEQ ID NO:2:

Lys-Thr-Thr-Lys-Ser

A peptide derived from human type-I collagen C-terminal (human type-I collagen DP) used in the present invention is represented by the following Chemical Formula 2:

[Chemical Formula 2]

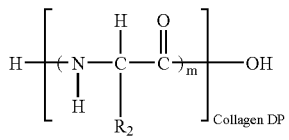

A peptide derived from human type-I collagen C-terminal is a peptide of continuous 5 to 35 amino acids consisting of a peptide of amino acids 212 to 216 in a peptide of amino acids 182 to 246 of human type-I collagen shown in SEQ ID NO:1 (m=5~35), and preferably a peptide of continuous 8 to 15 amino acids consisting of a peptide of amino acids 212 to 216 in a peptide of amino acid shown in SEQ ID NO:1, and more preferably, a peptide of SEQ ID NO:2 (m=5), a peptide of SEQ ID NO:3 (m=7), or a peptide of SEQ ID NO:4 (m=10). More specifically, the peptide derived from human Type-I collagen C-terminal comprises all of a peptide of SEQ ID NO:2; a peptide of amino acids 211 to 217, SEQ ID NO:3 (human Type-I collagen DP 211-217, Try-Lys-Thr-Thr-Lys-Ser-Ser); or a peptide of amino acids 210 to 219, SEQ ID NO:4 (human Type-I collagen DP 210–219, Val-Ile-Tyr-Lys-Thr-Thr-Lys-Ser-Ser-Arg-Leu.

Various human body diseases are caused by abnormal activities of cell proteins. As a result, there has been much worldwide attention recently on ways to develop materials that are capable of treating fatal human body diseases by controlling activities of these proteins. However, peptide and protein, despite having superior selectivity and usefulness for physical action to other compounds, are difficult to use in practice as effective drug delivery means because it is difficult to directly deliver these elements inside a cell.

In order to solve these problems, a relatively new protein penetration technology for effectively penetrating various bio-functioning proteins into cells has been used to directly and effectively deliver or absorb material required for the treatment of human diseases. Typical protein penetration technology uses a property of the Tat peptide, which is a type of protein of the Human Immunodeficiency Virus (HIV) type-1 that is self-penetrating, in which the Tat peptide spontaneously passes through a cell membrane for easy penetration such that transportation into the cell is realized. Such a capability is present due to the property of the protein transduction domain that is a middle region of the Tat peptide sequence, the exact mechanism of which has not yet been determined (Frankel, A. D. and Pabo, C. O. (1998) Cell 55, 1189–1193. Green, M. and Loewenstein, P. M. (1988) Cell 55, 1179–1188, Ma. M. and Nath, A. (1997) J. Virol. 71, 2495–2499. Vives, E., Brodin, P. and Lebleu, B. (1997) J. Biol. Chem. 272,16010–16017.)

The present inventors, following close observation of the cell-penetration property of the Tat peptide, covalently bonded skin-activating ingredients such as a human Type-collagen C-terminal derived peptide to a Tat peptide having a self penetration signal. This resulted in the fusion peptide being directly and effectively penetrated into cutaneous cells.

The "Self cell-penetrating Tat peptide" used herein refers to the Tat peptide itself or a peptide derived therefrom, and the Tat peptide or a peptide derived therefrom refers to a peptide having the cell-penetration property alone or in combination with a material bound thereto.

Specifically, one of the main features of the Tat peptide of HIV (human immunodeficiency virus) Type-1 is that of possessing a signal for opening the lipid barrier to be penetrated by the peptide sequence region in the N-terminal of the total protein. The sequence is as follows, and is also shown in SEQ NO:5:

Arg-Lys-Lys-Arg-Arg-Gln-Arg-Arg-Arg (or RKKRRQRRR).

Because amino acids comprising the Tat peptide such as lysine (hereinafter referred to as Lys or K), arginine (Arg or R), glutamine (Gln or Q), etc. have amine groups and carboxy groups, the self cell-penetrating Tat peptide can be bound to a human Type-I collagen C-terminal derived peptide by esterification with a carboxylic group through reaction with alcohol. Typical examples of self cell-penetrating Tat peptides (n=9) include a Tat peptide of SEQ ID NO:5 (Arg-Lys-Lys-Arg-Arg-Gln-Arg-Arg-Arg or RKKRRQRRR), a Tat peptide of SEQ ID NO:6 (Lys-Lys-Lys-Lys-Lys-Lys-Lys-Lys-Lys or KKKKKKKKK), a peptide of SEQ ID NO:7 (Arg-Arg-Arg-Arg-Arg-Arg-Arg-Arg-Arg or RRRRRRRRR), etc. The self cell-penetrating Tat peptides can be bound to human type-I collagen DP by condensation.

The self cell-penetrating Tat peptide is represented by the following Chemical Formula 3:

[Chemical Formula 3]

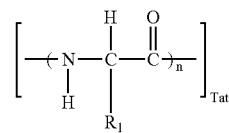

In the formula, $R_1$ is one or more substituent selected from the group consisting of side chains of glutamine (Gln), lysine (Lys), arginine (Arg), and glycine (Gly). The Tat peptide is a peptide consisting of 4 to 12 amino acids, and more preferably a peptide consisting of one or more amino acid selected from the group consisting of lysine and arginine. In addition, n is an integer from 4 to 12, preferably from 8 to 10, and most preferably n is 9.

The present invention provides a method for preparing a fusion peptide, in which a self cell-penetrating Tat peptide is bound to a peptide derived from human Type-collagen C-terminal (Tat-human Type-collagen DP).

More specifically, the Tat-human Type-collagen DP fusion peptide of the present invention can be prepared by the following methods.

The first method is a biological method using a recombinant expression vector. This method for preparing a Tat-HPTDP fusion peptide includes the steps of (a) cloning a Tat gene of HIV-1 by PCR (polymer chain reaction) of the N-terminal with a self penetration signal region from pSVC21, which is an expression vector comprising the HIV-1 Tat gene, in a pET vector, which is a protein expression vector comprising a 6 His tag, to prepare a vector capable of expressing a fusion protein; and (b) mass-expressing recombinant His-Tat-human Type-collagen DP peptide in E. coli using the pET-Tat expression vector, then performing separation and purification.

The second method is a method for preparing a Tat-human Type-collagen DP fusion peptide comprising the steps of integrating a target protein, for example catalase or superoxide dismutase (SOD), etc. into a pET-Tat-human Type-collagen DP expression vector to mass-express His-Tat-human Type-collagen DP fusion protein, then performing separation and purification.

The third method is a method for synthesizing a pure Tat-human Type-collagen DP fusion peptide using an organosynthesizer for peptide synthesis. This method is referred to as Merrifield solid-phase peptide synthesis (J. Am. Chem. Soc. 85, 2149–2154(1963)), during which the Tat-human Type-collagen DP fusion protein is synthesized by condensation of the (a) C-terminal of the amino acid of the Tat-human Type-collagen DP fusion peptide, which includes a Tat peptide having one or more amino acid selected from the group consisting of Gln, Lys, Arg, and Gly, and (b) monomers with N-terminal reactivity using a peptide synthesizer (Model 431A from ABI Company).

Solid phase synthesis starts by coupling an α-amino protected amino acid to an appropriate resin from an amino acid of a carboxy terminal. The α-amino protected amino acid is coupled to a hydroxy methyl resin or a chloro methylated resin through an ester bond. As an α-amino protecting group, Fmoc (9-fluorenyl methoxycarbonyl) or Boc (t-butyloxycarbonyl) is used. The Fmoc-protected amino acid is purchased from Pharmacia Company or Calbiochem Company. Examples of an amino acid having a reactive amino acid residue include an amino group of Arg residue or a reactive residue of Gly, Lys, or Gln, and Fmoc-amino acid protected with an appropriate group such as trityl (Trt), 4-methoxy-2,3-trimethylbenzene sulfunyl (MRT), tert-butyl (t-Bu). Peptide is synthesized by sequentially coupling an α-amino protected amino acid to an amino terminal of a peptide chain attached to a solid support resin after activation. After synthesis, the peptide is cut from the resin, and the protecting group is removed with a reagent such as trifluoroacetic acid (TFA). The peptide is separated from the TFA solution by filtration, centrifugation, or extraction with diethylether, and the peptide can be purified by high performance liquid chromatography (HPLC) or other methods.

The Tat-human Type-collagen DP fusion peptide represented by Chemical Formula 1 and prepared according to the present invention can be used as a skin anti-aging agent having superior chemical stability, that provides long-lasting anti-aging effects for the skin by the benefits obtained through synthesis of collagen and hyaluronic acid, and that is safe to use. A detailed activity evaluation of the anti-aging agent will be described in the Examples to follow.

The present invention provides a skin anti-aging cosmetic composition comprising a compound represented by Chemical Formula 1.

The composition of the present invention comprises 0.000001 to 5.0 wt % of the compound represented by Chemical Formula 1. If the amount of the compound is less than 0.000001 wt % of the total composition, substantial anti-aging effects cannot be expected, while if the amount of the compound exceeds 5.0 wt %, the compound negatively affects the stability of the product and the form of the preparation.

The form of the final product is not limited to any specific type, and it is possible to use common cosmetic forms. For example, the composition of the present invention can be prepared in the form of an external ointment, toner, lotion, nutrition cream, massage cream, essence, pack, emulsion, or oil gel.

When prepared as an external ointment, the composition comprises 50.0 to 97.0 wt % of Vaseline and 0.1 to 5.0 wt % of polyoxyethyleneoleyl-ether phosphate in addition to the compound represented by Chemical Formula 1. When prepared as a toner, the composition comprises 1.0 to 10.0 wt % of polyalcohol such as propylene glycol, glycerine, etc. and 0.05 to 2.0 wt % of a surfactant such as polyethyleneoleylether, polyoxyethylene hardened castor oil, etc. Further, when prepared as a lotion or nutrition cream, the composition comprises 5.0 to 20.0 wt % of oil such as squalene, Vaseline, and octyidodecanol, and 3.0 to 15.0 wt % of waxy ingredients such as cetanol, stearylalcohol, paraffin, etc., in addition to the active ingredient of the compound represented by Chemical Formula 1. When prepared as an essence, the composition comprises 5.0 to 3.0 wt % of polyalcohol such as glycerine, propyleneglycol, etc. In the case where the present invention is prepared as a massage cream, the composition comprises 30.0 to 70.0 wt % of oil such as flow paraffin, Vaseline, isononylisononanoate, etc., in addition to the active ingredient of the compound of Chemical Formula 1. The pack may be prepared in the form of a peel-off pack, in which case the composition comprises 5.0 to 20.0 wt % of polyvinylalcohol, or the pack may be prepared in the form of a wash-off pack, in which case the composition comprises common emulsifying cosmetics and 5.0 to 30.0 wt % of a pigment such as kaolin, talc, zinc oxide, or titan dioxide.

In addition, it is possible to mix (in an appropriate amount) ingredients commonly used in general skin cosmetics such as an oily substance, water, a surfactant, a moisturizer, low alcohol, a thickener, a chelating agent, pigment, an antiseptic, perfume, etc. with the skin anti-aging cosmetic composition comprising the compound represented by Chemical Formula 1 of the present invention. A transdermal absorption test, a skin stimulation test, a synthesis of collagen and hyaluronic acid effects test, and an anti-aging effects test were carried out in order to confirm physical activities of the compound of the present invention. The results of the tests revealed that the compound of the present invention has superior transdermal absorbency, superior synthesis of collagen and hyaluronic acid, and exceptional anti-aging effects. Since the compound of the present invention does not cause irritation, and has superior activity and skin absorption to thereby provide superior anti-aging effects, it can be used in any form that cosmetics are normally found such as a cream, lotion, gel, etc.

The present invention will be explained in more detail with reference to the following Examples. However, it is to be noted that the present invention can be utilized in various ways and is not intended to be confined to the examples.

EXAMPLE

Example 1

Preparation of a Tat-human Type-I collagen DP fusion Peptide (KKKKKKKKKKTKS) (SEQ ID NO: 9)

(1) Preparation of a Tat-Human Type-Collagen DP Fusion Peptide

The Tat-human Type-I collagen DP fusion peptide used in the present invention is a peptide consisting of 14 amino acids having the sequence KKKKKKKKKKTKS (SEQ ID NO: 9), and it is synthesized by a solid phase peptide synthesis method using a peptide autosynthesizer (Applied Biosystems Model 431A). 0.25 mmol of a parahydroxy methylphenyloxymethyl polystyrene (HMP) resin was introduced in a reaction vessel (38 mL), and Fmoc-amino acid of a carboxy terminal of the peptide to be synthesized was introduced to start synthesis. A cartridge containing 1 mmol of Fmoc-amino acid was arranged in a guideway in the sequence starting from the carboxy terminal amino acid and ending at the terminal amino acid. Next, metal openings of the cartridge were removed and empty cartridges were laid on the first and the last amino acids.

Before peptide synthesis, a parameter was edited according to the standard scale Fmoc coupling protocol developed by ABI Company, and peptide synthesis was conducted according to the autosynthesis menu (ABI User's Manual. Jan, 1992). When using the standard scale Fmoc, deprotection was conducted for 21 minutes using 20% piperidine diluted with N-methyl pyrrolidine (NMP). Also performed were washing with NMP for 9 minutes and coupling for 71 minutes. 1-hydroxy-benzotriazole (HOBT) was used for the coupling, and washing with NMP was then conducted for an additional 7 minutes.

(2) Separation and Purification of a Tat-Human Type-collagen DP Fusion Peptide

After synthesis, the Tat-human Type-collagen DP fusion peptide was separated from the solid support using trifluoroacetic acid (TFA), as outlined in the ABI Company manual (Introduction to Cleavage Techniques, P6–19(1990)). Specifically, after synthesis, a peptide-attached resin was introduced into a round-bottomed flask and refrigerated, and then 0.75 g of crystal phenol, 0.25 mL of 1,2-ethandithiol (EDT), 0.5 mL of thioanisol, 0.5 mL of distilled water, and 10 mL of TFA were introduced in the flask and reacted at room temperature for 1 to 2 hours with openings of the flask closed. After reaction, the resin and reaction solution were filtered through a sintered glass funnel under low vacuum to separate the resin and peptide solution. The flask and glass funnel were washed with 5~10 mL of dichloromethane (DCM) to mix the solution with the peptide solution, and 50 mL or more of cool diethylether were added to obtain a peptide precipitate. The precipitate was filtered through a funnel under low vacuum, and precipitate gathered on the funnel was dried, dissolved in 30% acetic acid, and lyophilized. The peptide obtained in this manner was purified through HPLC (High Performance Liquid Chromatography). A C18 analytical column (Pharmacia) was used, and buffer solution A was equilibrated with 10% acetonitrile+ 0.05% TFA, and the peptide was eluted from buffer solution B using 80% acetonitrile+0.05% TFA. As a result, a highly purified peptide was obtained, with the yield of synthesis being approximately 30.5%.

Example 2

Collagen Synthesis Effects Test

In order to measure the usefulness of the Tat-human Type-collagen DP prepared in Example 1 as a skin anti-aging agent, it was tested by comparing the preparation with ascorbic acid, which is known to be a material having an exceptional collagen synthesis effect.

In this test, a human fibroblast of the same number was cultured on a 24-well plate for 24 hours, and the sample as a concentration of $10^{-4}$ to $10^{-7}$ was applied thereto. After 2 hours, proline introduced tridium was applied thereto and a resulting mixture was cultured for 24 hours. Next, an amount of collagen newly-synthesized and newly-secreted from fibroblast was measured a cpm (count per minute) of proline introduced tridium using a medium, and an amount of csp (collagenous sensitive protein) was calculated. A comparative measurement of the collagen synthesis effect was then performed (David F. W. and Wilson Harvey, *Analytical Biochemistry* (1979); 96, 220 224, Atsushi Hatamochi, Masashi Ono, Hiroaki Ueki, and Masayoshi Namba., *J. Invest Dermatol*. (1991) 96, 473 477).

Example 3

Anti-Aging Effects

In order to examine anti-aging effects of the Tat-human Type-collagen DP prepared in Example 1, an O/W emulsion comprising the compound of Chemical Formula 1 of the present invention and a control were each applied to human subjects. In particular, the O/W emulsion and control were coated on wrinkles on the outer corners of the eyes (i.e., crow's-feet) of 29 women in their thirties. Application was performed for 3 months, one time each day. Visual observation of anti-aging effects, if any, was performed and ranked according to a scale of four possibilities—no improvement, little improvement, medium improvement, and significant improvement.

Results of the above experiment revealed that the compound represented by Chemical Formula 1 used in the present invention exhibits anti-aging effects on crow's-feet. It was therefore determined that the compound represented by Chemical Formula 1 used in the present invention would produce anti-aging effects when used in an ointment on the skin.

Example 4

Transdermal Absorption (Penetration into Skin Cells) Test

Penetration of a compound, agent, etc. into skin cells is commonly referred to as transdermal absorption, and this will be the term used herein. The transdermal absorption test was conducted using the fusion peptide prepared in Example 1 (Reference: Lehman P A, Slattery J T, Franz T J. Percutaneous absorption of retinoids: Influence of vehicle, light exposure, and dose, J. Invest Dermatol., 91; 56–61. 1998).

Specifically, skin on the back of a female nude mouse 8 weeks of age was cut to a specific depth and to an area of 1.7 $cm^2$, and the fusion peptide was applied thereto. After 24 hours, the receptor solution and material absorbed in the skin in the back of the mouse were extracted with a transdermal absorption measuring instrument (Franz cell), and quantitatively analyzed using high performance liquid chromatography (HPLC) and liquid chromatography mass (LC mass) techniques. That is, these techniques were used to measure the amount of the compound of Chemical Formula 1 of the present invention that underwent transdermal absorption. Results of this test revealed that the compound of Chemical Formula 1 of the present invention exhibits a superior transdermal absorption capability. Example 5: Allergy Test of a Tat-human Type-I collagen DP fusion peptide (LLNA) (SEQ ID NO: 10)

An experiment using ethanol as a carrier was selected for a safety test of the compound of Chemical Formula 1 when used as a cosmetic raw material [Reference: Kimber (1990): Identification of contact allergens using the murinelocal lymph node assay, J. Appl. Toxicol. 10(3); 173–180]. A control that uses cosmetic material for an anti-aging agent and the compound of Chemical Formula 1 were prepared in 0.5% and 1.0% solutions. 50 µl of the solution was applied to both ears of Balb/c mice for 3 days, and then the auricular lymph nodes were removed from the mice. The lymph nodes were pulverized to a monocell state, and radioisotope [3H]-methylthymidine was added thereto, after which a resulting material was cultured for 24 hours. Subsequently, amplification of cells (dpm, disintegrations per minute) was measured using a β-scintillation counter (Beckman LS 6000 TA, USA). The results of the test indicate that the compound of Chemical Formula 1 of the present invention exhibits a lower possibility of allergy induction than the control.

Example 6

Skin Irritation Test of a Tat-human Type-Collagen DP Fusion Peptide

In order to test skin irritation of the compound of Chemical Formula 1, a patch test using guinea pigs was conducted [Reference: Draize, J. H. (1959): Dermal toxicity. Assoc. Food and Drug Officials, US. Appraisal of the safety of chemicals in Food, Drugs, and Cosmetics., pp 46–59, Texas State Dept. of Health, Austin, Tex. Federal Register (1973): Method of testing primary irritant substances 38(187): pp 1500–1541]. The compound represented by Chemical Formula 1 was prepared in an O/W emulsion of various concentrations. Fur on the back of the guinea pigs where the sample was to be coated was removed, and the area was allowed to adapt to the surroundings for 24 hours in order to minimize skin irritation that may be caused by the removal of the fur.

Next, a sample coating region was established (1.5 cm×1.5 cm), a sample and gauze were applied thereto, and the coated region was sealed with a thin paper of solid material in order to prevent loss, after which the sealing material was held firmly in place with an elastic bandage. The guinea pigs were maintained in this state for 48 hours then all the applied materials were removed. At two different time periods of 2 hours and 24 hours after removal of the closed patch (50 hours and 72 hours after patch application), the degree of irritation was determined and indicated by an irritation index (P11: primary cutaneous irritation index) and by an irritation degree scale. The results of this test are shown in Table 1.

TABLE 1

| Sample | Concentration (%) | Irritation Index (PII) | Irritation Degree |
|---|---|---|---|
| Control | — | 0.50 | Minute irritation |
| Compound represented by the Chemical Formula 1 | 0.01 | 0.52 | Minute irritation |
| | 0.1 | 0.53 | Minute irritation |
| | 0.5 | 0.53 | Minute irritation |

It is evident from Table 1 that the compound represented by Chemical Formula 1 may be safely used on the skin without causing irritation.

Example 7

Cytotoxicity Test of a Tat-Human Type-collagen DP Fusion Peptide

In order to identify the safety of the compound of Chemical Formula 1 when used as a cosmetic raw material, V79-4 cells (Chinese hamster, continuous cell line of lung tissue fibroblast) were cultured and an MTT test was conducted to test cytotoxicity for the compound [Reference: Mossaman T. (1983). Rapid colorimetric assay for cellular growth & survival: application to proliferation & cytotoxicity assays. Journal of Immunological Methods 65, 55–63). The test revealed that the compound of Chemical Formula 1 gradually showed very weak toxicity at a concentration of 0.1 (%, w.v) or more, and a negligent level of toxicity at a concentration of 0.01 or less.

The present invention provides a Tat-human Type-collagen DP fusion peptide, in which a self cell-penetrating Tat peptide having a self penetration signal is bound to a human Type-collagen C-terminal derived peptide. The present invention also provides a skin anti-aging agent comprising the peptide. The anti-aging agent of the present invention exhibits superior skin absorption, does not cause irritation, and has superior synthesis of collagen and hyaluronic acid effects. The anti-aging agent has anti-aging effects and durability to the existing human Type-collagen C-terminal derived peptide, due to the presence of the self cell-penetrating Tat peptide.

The invention claimed is:

1. A fusion peptide, in which a peptide selected from the group consisting of a peptide of SEQ ID NO: 6 and a peptide of SEQ ID NO: 7, is bound to N-terminal of a human Type-I collagen C-terminal derived peptide,
   wherein the human Type-I collagen C-terminal derived peptide is a peptide consisting of continuous 5 to 35 amino acids comprising a peptide of amino acids 212 to 216 in a peptide of amino acids 182 to 246 of human type-I collagen shown in SEQ ID NO:1.

2. The fusion peptide according to claim 1, wherein the human Type-I collagen C-terminal derived peptide is a peptide of continuous 8 to 15 amino acids comprising a peptide of amino acids 212 to 216 in a peptide of amino acid shown in SEQ ID NO:1.

3. The fusion peptide according to claim 1, wherein the human Type-I collagen C-terminal derived peptide is selected from the group consisting of a peptide as shown in SEQ ID NO:2, a peptide as shown in SEQ ID NO:3, and a peptide of as shown in SEQ ID NO:4.

4. A method for preparing the fusion peptide of claim 1 by solid phase peptide synthesis.

5. A method for preparing the fusion peptide of claim 1 by a biological method using recombinant DNA technology.

6. A skin wrinkles improving cosmetic composition comprising the fusion peptide of claim 1 as an active ingredient.

7. The skin wrinkles improving cosmetic composition according to claim 6, wherein the fusion peptide of claim 1 is contained in an amount of 0.000001 to 5.0 wt %.

* * * * *

SEQUENCE LISTING

<160> NUMBER OF SEQ ID NOS: 10

<210> SEQ ID NO 1
<211> LENGTH: 65
<212> TYPE: PRT
<213> ORGANISM: Artificial Sequence
<220> FEATURE:
<223> OTHER INFORMATION: HUMAN TYPE-I COLLAGEN DP 182-246 SEQUENCE

```
<400> SEQUENCE: 1

Ala Glu Gly Asn Ser Arg Phe Thr Tyr Ser Val Thr Val Asp Gly Cys
 1               5                  10                  15

Thr Ser His Thr Gly Ala Trp Gly Lys Thr Val Ile Glu Tyr Lys Thr
            20                  25                  30

Thr Lys Ser Ser Arg Leu Pro Ile Ile Asp Val Ala Pro Leu Asp Val
        35                  40                  45

Gly Ala Pro Asp Gln Glu Phe Gly Phe Asp Val Gly Pro Val Cys Phe
    50                  55                  60

Leu
 65

<210> SEQ ID NO 2
<211> LENGTH: 5
<212> TYPE: PRT
<213> ORGANISM: Artificial Sequence
<220> FEATURE:
<223> OTHER INFORMATION: HUMAN TYPE I COLLAGEN DP SEQUENCE

<400> SEQUENCE: 2

Lys Thr Thr Lys Ser
 1               5

<210> SEQ ID NO 3
<211> LENGTH: 7
<212> TYPE: PRT
<213> ORGANISM: Artificial Sequence
<220> FEATURE:
<223> OTHER INFORMATION: HUMAN TYPE I COLLAGEN DP SEQUENCE

<400> SEQUENCE: 3

Tyr Lys Thr Thr Lys Ser Ser
 1               5

<210> SEQ ID NO 4
<211> LENGTH: 11
<212> TYPE: PRT
<213> ORGANISM: Artificial Sequence
<220> FEATURE:
<223> OTHER INFORMATION: HUMAN TYPE I COLLAGEN DP SEQUENCE

<400> SEQUENCE: 4

Val Ile Tyr Lys Thr Thr Lys Ser Ser Arg Leu
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: TAT PEPTIDE SEQUENCE

<400> SEQUENCE: 5

Arg Lys Lys Arg Arg Gln Arg Arg Arg
 1               5

<210> SEQ ID NO 6
<211> LENGTH: 9
<212> TYPE: PRT
<213> ORGANISM: Artificial Sequence
<220> FEATURE:
<223> OTHER INFORMATION: TAT PEPTIDE SEQUENCE

<400> SEQUENCE: 6
```

-continued

```
Lys Lys Lys Lys Lys Lys Lys Lys Lys
1               5

<210> SEQ ID NO 7
<211> LENGTH: 9
<212> TYPE: PRT
<213> ORGANISM: Artificial Sequence
<220> FEATURE:
<223> OTHER INFORMATION: TAT PEPTIDE SEQUENCE

<400> SEQUENCE: 7

Arg Arg Arg Arg Arg Arg Arg Arg Arg
1               5

<210> SEQ ID NO 8
<211> LENGTH: 14
<212> TYPE: PRT
<213> ORGANISM: Artificial Sequence
<220> FEATURE:
<223> OTHER INFORMATION: TAT-HUMAN TYPE I COLLAGEN DP SEQUENCE

<400> SEQUENCE: 8

Lys Lys Lys Lys Lys Lys Lys Lys Lys Lys Thr Thr Lys Ser
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Tat-human Type-I collagen DP fusion peptide

<400> SEQUENCE: 9

Lys Lys Lys Lys Lys Lys Lys Lys Lys Lys Thr Lys Ser
1               5                   10

<210> SEQ ID NO 10
<211> LENGTH: 4
<212> TYPE: PRT
<213> ORGANISM: Artificial Sequence
<220> FEATURE:
<223> OTHER INFORMATION: Tat-human Type-I collagen DP fusion peptide

<400> SEQUENCE: 10

Leu Leu Asn Ala
1
```